United States Patent [19]

Shimizu et al.

[11] 4,051,129

[45] Sept. 27, 1977

[54] PROCESS FOR PREPARING 7-METHOXYCEPHALOSPORIN COMPOUNDS

[75] Inventors: Bunji Shimizu; Akio Saito; Masakatsu Kaneko; Hiroaki Yanagisawa; Hideo Nakao, all of Hiromachi, Japan

[73] Assignee: Sankyo Company Limited, Tokyo, Japan

[21] Appl. No.: 630,816

[22] Filed: Nov. 11, 1975

[30] Foreign Application Priority Data

Nov. 30, 1974 Japan ................. 49-138799

[51] Int. Cl.$^2$ ................. C07D 501/04; C07D 501/36; C07D 501/28; C07D 501/22
[52] U.S. Cl. ................................................. 544/21
[58] Field of Search ...................... 260/243 C

[56] References Cited

U.S. PATENT DOCUMENTS 3,862,182  1/1975  Johnston .................. 260/243 C
3,947,413  3/1976  Christensen et al. ........... 260/243 C Primary Examiner—Nicholas S. Rizzo
Assistant Examiner—David E. Wheeler
Attorney, Agent, or Firm—Flynn & Frishauf

[57] ABSTRACT

A process for preparing 7α-methoxycephalosporin compounds which comprises reacting a salt of a 7β-benzylideneamino-7α-methoxy-3-cephem-4-carboxylic acid with a hydrazine compound to give a salt of a 7β-amino-7α-methoxy-3-cephem-4-carboxylic acid and reacting the latter compound with a carboxylic acid or its reactive derivative. The products are useful as antibacterial agents.

7 Claims, No Drawings

PROCESS FOR PREPARING 7-METHOXYCEPHALOSPORIN COMPOUNDS

This invention relates to a novel process for preparing 7-methoxycephalosporin derivatives.

More particularly, this invention relates to a process for the preparation of 7α-methoxy-3-cephem-4-carboxylic acid derivatives having the formula

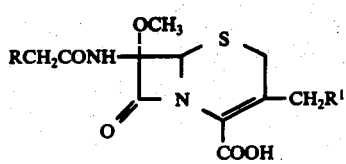
(I)

wherein R represents cyanomethylthio group, 1-cyanoethylthio group, azidomethylthio group, propargylthio group, 2-hydroxyethylthio group, 2,3-dihydroxypropylthio group, methylsulfonyl group, ethylsulfonyl group, cyanoethylsulfonyl group, 3-isoxazolyloxy groups, 3-isoxazolylthio group, 2-(1,3,4-thiadiazolyl)thio group, 2-imidazolylthio group or sydnon-3-yl group and $R^1$ is acetoxy group, carbamoyloxy group or 1-methyl-1H-tetrazol-5-ylthio group or salts thereof.

All of the 7-methoxycephalosporin derivatives having the formula (I) or their salts are novel and exhibit broad antibacterial spectra, especially satisfactory antibacterial activities against both gram-positive and -negative organisms as compared with the hitherto known 7-methoxycephalosporin derivatives.

As the method for preparing 7-methoxycephalosporins, there have heretofore been known (a) a method comprising diazotizing 7-aminocephalosporanic acid and converting the 7-position substituent to an alkoxy group (Japanese Pat. Pro. Pub. 931/72), (b) a method comprising reacting a 7-benzylideneamino compound with a dialkyl peroxide or the like (Japanese Pat. Pro. Pub. 42691/72), (c) a method comprising alkylthionating or fluorinating and acylating a 7-benzylideneamino compound and converting the 7-position substituent to an alkoxy group [J. O. C. 38 943 and 2857, (1973)], (d) a method comprising N-chlorinating the 7-acylamino group, converting the N-chlorinated group to an acylimino group and adding methanol thereto [J. A. C. S. 95 2403, (1973)], etc. Each of these known methods, however, involves problems or difficulties.

It is thus an object of this invention to provide a novel process for preparing the 7α-methoxycephalosporin derivatives which can be carried out more simply and hardly produce by-product as compared with the prior methods.

According to the present invention, the 7α-methoxycephalosporin derivative having the formula (I) may be prepared by reacting a 7β-benzylideneamino-7α-methoxy-3-cephem-4-carboxylic acid derivative having the formula

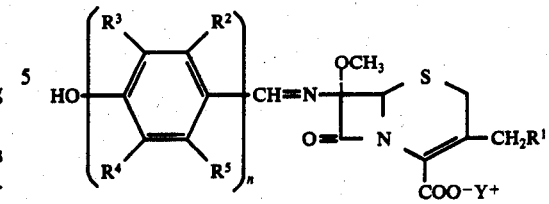
(II)

wherein $R^1$ is the same as defined above, $R^2$, $R^3$, $R^4$ and $R^5$ may be the same or different and each represents hydrogen atom, an alkyl group having 1–4 carbon atoms, an alkoxy group having 1–4 carbon atoms, a halogen atom, cyano group or an alkoxycarbonyl group having 1–4 carbon atoms in the alkoxy moiety, or $R^2$ and $R^3$ or $R^4$ and $R^5$ may be linked together to form a saturated, unsaturated or aromatic ring, n is an integer of 1 or 2 and Y+ is a cation with a hydrazine compound to give a 7β-amino-7α-methoxy-3-cephem-4-carboxylic acid derivative having the formula

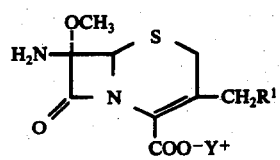
(III)

wherein $R^1$ and Y+ are the same as defined above and reacting the latter compound with a carboxylic acid having the formula $RCH_2COOH$      (IV)

wherein R is the same as defined above or its reactive derivative.

In the above formula (II), the groups $R^2$ to $R^5$ may be the same or different and each represents preferably hydrogen atom; a straight or branched alkyl group having 1–4 carbon atoms such as methyl, ethyl, propyl, isopropyl and tert.-butyl; a straight or branched alkoxy group having 1–4 carbon atoms such as methoxy, ethoxy, propoxy, isopropoxy and tert.-butoxy; a halogen atom such as chlorine and bromine; cyano group; an alkoxycarbonyl group having 1–4 carbon atoms in the alkyl moiety such as methoxycarbonyl, ethoxycarbonyl and tert.-botoxycarbonyl. $R^2$ and $R^3$ or $R^4$ and $R^5$ may be linked together to form a saturated, unsaturated or aromatic ring such as cyclopentane, cyclohexane, cycloheptane and benzene. n is an integer of 1 or 2 and, when n is 2, for example, biphenyl, binaphthalene or p-(4-naphthyl)benzene may be formed. $R^3$ and $R^4$ may be suitably selected from a sterically hindered alkyl group such as isopropyl and tert.-butyl. Y+ is a cation suitably selected from the group consisting of an alkali metal ion and an ammonium ion having the formula

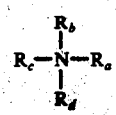

wherein $R_a$, $R_b$, $R_c$ and $R_d$ may be the same or different and each represents hydrogen atom; a straight or branched alkyl group having 1–8 carbon atoms such as methyl, ethyl, propyl, isopropyl, tert.-butyl, octyl and tert.-octyl; a cycloalkyl group having 5–7 carbon atoms such as cyclopentyl, cyclohexyl and cycloheptyl; phenyl group; or a phenylalkyl group having 1–4 carbon atoms in the alkyl moiety such as benzyl or phenethyl; or $R_a$ and $R_b$ may be linked together with N to form a saturated heterocyclic ring such as pyrrolidine, piperidine and morpholine; or $R_a$, $R_b$ and $R_c$ may be linked together with N to form a heteroaromatic ring such as pyridine, picolin, lutidine, quinoline, quinaldine and pyrimidine. The most preferable cation as $Y^+$ is lithium, sodium, tert.-butylammonium, tert.-octylammonium, dicyclohexylammonium, diisopropylammonium, triethylammonium and trimethylbenzylammonium ions.

In carrying out the process of this invention, the first step may be conducted by contacting the compound (II) with a hydrazine compound in an inert organic solvent. The solvent may be employed without any critical limitation in this reaction so far as it does not take part in the reaction. As the solvents are mentioned, for example, a lower alkanol such as methanol, ethanol, propanol, isopropanol, butanol, isobutanol, pentanol; an aromatic hydrocarbon such as benzene, toluene and xylene; a halogenated hydrocarbon such as chloroform and methylene chloride; dimethylformamide and dimethylacetamide and the like.

In this reaction non-substituted and substituted hydrazines may be employed without any particular limitation. Representative examples of the hydrazine compound include phenylacetic acid hydrazine, hydrazine, hydrazine hydrate, phenylhydrazine, 2,4-dinitrophenylhydrazine, pyridylacetohydrazide chloride (Girard reagent P), trimethylaminoacetohydrazide chloride (Girard reagent T) and the like.

The reaction temperature is not particularly critical and the reaction may effectively proceed at room temperature and also at above or below the room temperature as well. The time required for the reaction may be varied mainly depending upon the starting material, the sort of the reagent and solvent employed, the reaction temperature and the like, but it may usually take about several tens of minutes. After the reaction is completed, the product may be recovered in a usual manner. The reaction mixture, however, may be employed in the next step as the starting material.

The second step may be carried out by contacting the compound (III) with the carboxylic acid (IV) or reactive derivative thereof in appropriate solvent.

As carboxylic acids having the formula (IV) are mentioned cyanomethylthioacetic acid, 1-cyanoethylthioacetic acid, azidomethylthioacetic acid, propargylthioacetic acid, methylsulfonylacetic acid, ethylsulfonylacetic acid, cyanoethylsulfonylacetic acid, 3-isoxazolyloxyacetic acid, 3-isoxazolylthioacetic acid, 2-(1,3,4-thiadiazolyl)thioacetic acid, 2-imidazolylthioacetic acid and sydnon-3-ylacetic acid. The reactive derivatives of the carboxylic acid (IV) may be halides of said acid such as acid chlorides, acid bromides and acid fluorides; azides of said acid; mixed acid anhydrides between those acids mentioned above and other fatty acids such as, for instance, alkyl chlorocarbonate; acid anhydrides; reactive esters such as, for instance, p-nitrophenyl ester, cyanomethyl ester, phthalimide ester or the like. When 2-hydroxyethylthioacetic acid, 2,3-dihydroxypropylthioacetic acid or their derivatives are used in this reaction, they should be reacted after protecting the hydroxy groups with a suitable protecting group such as tetrahydropyranyl group. In the case of using the above-mentioned carboxylic acid itself, the reaction can be effected in the presence of carbodiimide such as N,N'-dicyclohexylcarbodiimide, carbonyldiimide such as carbonyldiimidazol and carbonylditriazol, alkoxyacetylene such as methoxyacetylene in the reaction medium. As to the solvent which may be employed in the reaction there is no particular limitation if it will not participate in the reaction. As examples of such solvents may be mentioned, for instance, a halogenated hydrocarbon such as chloroform, methylene chloride and ethylene chloride; a lower alkyl ketone such as acetone and methylethyl ketone; an acetic acid ester such as ethyl acetate and butyl acetate; an ether such as diethyl ether, tetrahydrofuran and dioxane; an aromatic hydrocarbon such as benzene and toluene; acetonitrile; dimethylformamide; dimethylacetamide; water and the like. A suitable solvent for the reaction can be selected depending upon the sort of the carboxylic acid employed by those in the art. The preferred carboxylic acid derivative for the reaction is an acid halide and in this case the reaction can be effectively carried out in the presence of an acid binding agent such as an inorganic or organic base. As inorganic bases are mentioned alkali and alkaline earth metal compounds which involve, for instance, the hydroxides such as sodium hydroxide, lithium hydroxide or potassium hydroxide; the carbonates such as sodium carbonate and potassium carbonates; the hydrogen carbonate such as sodium hydrogen carbonate and lithium hydrogen carbonate. As organic bases are exemplified the tertiary amines such as triethylamine, tributylamine, diethylaniline, N-methylpyperidine, N-methylmorpholine; pyridine; quinoline and the like. The reaction temperature is not particularly critical and the reaction may usually be effected at 0° C to a room temperature, but other temperatures than those may also be used. The time required for the reaction may be varied mainly depending upon the sort of the carboxylic acid (IV) and its derivative, the sort of 7-amino-7α-methoxycephem compound (III), the reaction temmperature employed and the like, but it may usually take several minutes to several tens of minutes. The reaction product can be recovered by a usual manner from the reaction mixture. For example, after the reaction is completed a lower alkanol such as methanol or diluted hydrochloric acid is added to the reaction mixture and the organic layer is extracted with aqueous disodium hydrogen phosphate solution, the extract is made acidic (pH 2) by an appropriate acid and reextracted with ethyl acetate and the like, the organic solvent layer is separated and dried, and the solvent is removed to afford the desired product. The conventional purification techniques such as recrystallization or column chromatography may be applied further in order to obtain a pure substance.

As the representative compounds obtained in this invention are mentioned the following:

3-acetoxymethyl-7β-cyanomethylthioacetamido-7α-methoxy-3-cephem-4-carboxylic acid,
3-acetoxymethyl-7β-propargylthioacetamido-7α-methoxy-3-cephem-4-carboxylic acid,
3-acetoxymethyl-7β-(3-isoxazolyloxy)acetamido-7α-methoxy-3-cephem-4-carboxylic acid,
3-acetoxymethyl-7β-(3-isoxazolylthio)acetamido-7α-methoxy-3-cephem-4-carboxylic acid,
3-acetoxymethyl-7β-azidomethylthioacetamido-7α-methoxy-3-cephem-4-carboxylic acid,
7β-(2-imidazolylthio)acetamido-7α-methoxy-3-(1-methyl-1H-tetrazol-5-yl)thiomethyl-3-cephem-4-carboxylic acid, 3-(1-methyl-1H-tetrazol-5-yl)thiomethyl-7β-2-(1,3,4-thiadiazolylthio)acetamido-7α-methoxy-3-cephem-4-carboxylic acid, 3-acetoxymethyl-7β-2-(1,3,4-thiadiazolylthio)acetamido-7α-methoxy-3-cephem-4-carboxylic acid.

3-acetoxymethyl-7β-(2-imidazolylthio)acetamido-7α-methoxy-3-cephem-4-carboxylic acid, 3-acetoxymethyl-7β-(2-imidazolylthio)acetamido-7α-methoxy-4-carboxylic acid, 7β-cyanomethylthioacetamido-7α-methoxy-3-(1-methyl-1H-tetrazol-5-yl)thiomethyl-3-cephem-4-carboxylic acid, 7β-azidomethylthioacetamido-7α-methoxy-3-(1-methyl-1H-tetrazol-5-yl)thiomethyl-3-cephem-4-carboxylic acid, 7β-propargylthioacetamido-7α-methoxy-3-(1-methyl-1H-tetrazol-5-yl)thiomethyl-3-cephem-4-carboxylic acid, 7β-(3-isoxazolyloxy)acetamido-7α-methoxy-3-(1-methyl-1H-tetrazol-5-yl)thiomethyl-3-cephem-4-carboxylic acid, 7β-(3-isoxazolylthio)acetamido-7α-methoxy-3-(1-methyl-1H-tetrazol-5-yl)thiomethyl-3-cephem-4-carboxylic acid, 3-acetoxymethyl-7β-cyanoethylsulfonyl-7α-methoxy-3-cephem-4-carboxylic acid, 7α-methoxy-7β-methylsulfonylacetamido-3-(1-methyl-1H-tetrazol-5-yl)thiomethyl-3-cephem-4-carboxylic acid, 7β-(syndon-3)acetamido-7α-methoxy-3-(1-methyl-1H-tetrazol-5-yl)thiomethyl-3-cephem-4-carboxylic acid, 3-carbamoyloxymethyl-7α-methoxy-7β-cyanoethylsulfonylacetamido-3-cephem-4-carboxylic acid, 7β-(2-hydroxyethylthio)acetamido-7α-methoxy-3-(1-methyl-1H-tetrazol-5-yl)thiomethyl-3-cephem-4-carboxylic acid, 3-acetoxymethyl-7β-(2,3-dihydroxypropylthio)acetamido-7α-methoxy-3-cephem-4-carboxylic acid, 7β-ethylsulfonyl-acetamido-7α-methoxy-3-(1-methyl-1H-tetrazol-5-yl)thiomethyl-3-cephem-4-carboxylic acid, 7β-(1-cyanoethyl)acetamido-7α-methoxy-3-(1-methyl-1H-tetrazol-5-yl)thiomethyl-3-cephem-4-carboxylic acid and the like.

These compounds exhibit satisfactory antibacterial properties. As especially excellent antibacterial compounds are mentioned the following:

7β-cyanomethylthioacetamido-7α-methoxy-3-(1-methyl-1H-tetrazol-5-yl)thiomethyl-3-cephem-4-carboxylic acid, 7β-(sydnon-3)acetamido-7α-methoxy-3-(1-methyl-1H-tetrazol-5-yl)thiomethyl-3-cephem-4-carboxylic acid, 7β-(1-cyanoethyl)-acetamido-7α-methoxy-3-(1-methyl-1H-tetrazol-5-yl)thiomethyl-3-cephem-4-carboxylic acid, 7β-methylsulfonylacetamido-7α-methoxy-3-(1-methyl-1H-tetrazol-5-yl)thiomethyl-3-cephem-4-carboxylic acid, 7β-(2-hydroxyethylthio)acetamido-7α-methoxy-3-(1-methyl-1H-tetrazol-5-yl)thiomethyl-3-cephem-4-carboxylic acid, 7β-ethylsulfonylacetamido-7α-methoxy-3-(1-methyl-1H-tetrazol-5-yl)thiomethyl-3-cephem-4-carboxylic acid, 7β-cyanoethylsulfonyl-acetamido-7α-methoxy-3-(1-methyl-1H-tetrazol-5-yl)thiomethyl-3-cephem-4-carboxylic acid, 3-carbamoyloxymethyl-7β-cyanomethylthioacetamido-7α-methoxy-3-cephem-4-carboxylic acid, 3-acetoxymethyl-7β-cyanomethylthio-7α-methoxy-3-cephem-4-carboxylic acid, 7α-methoxy-3-(1-methyl-1H-tetrazol-5-yl)thiomethyl-7β-propargylmethylthioacetamido-3-cephem-4-carboxylic acid, 7β-azidomethylthioacetamido-7α-methoxy-3-(1-methyl-1H-tetrazol-5-yl)thiomethyl-3-cephem-4-carboxylic acid, 7β-(3-isoxazolyloxy)acetamido-7α-methoxy-3-(1-methyl-1H-tetrazol-5-yl)thiomethyl-3-cephem-4-carboxylic acid, 7β-(3-isoxazolylthio)acetamido-7α-methoxy-3-(1-methyl-1H-tetrazol-5-yl)thiomethyl-3-cephem-4-carboxylic acid, 7β-azidomethylthioacetamido-3-carbamoyloxymethyl-7α-methoxy-3-cephem-4-carboxylic acid, 3-acetoxymethyl-7β-(3-isoxazolylthio)acetamido-7α-methoxy-3-cephem-4-carboxylic acid and the like.

These compounds may be converted by a usual manner into atoxic salts and preferably alkali metal salts.

Antibacterial properties of these compounds are shown as follows:

Minimum Inhibitory Concentration (mcg/ml)

RCH₂CONH—[β-lactam with OCH₃, S, N, CH₂R¹, COOH substituents]

| Compounds | | I | | II | III | IV | | V | VI |
|---|---|---|---|---|---|---|---|---|---|
| R | R' | A | B | A | B | | A | B | |
| NCCH₂S— | -S-[1-methyl-tetrazol-5-yl] | 0.2 | 0.8 | 0.8 | 0.8 | 0.8 | 0.8 | >200 | 1.5 | 0.2 |

-continued

Minimum Inhibitory Concentration (mcg/ml)

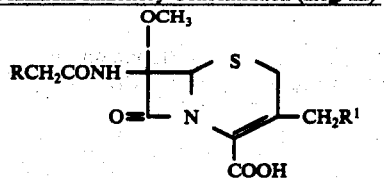

| Compounds | | I | | II | III | IV | | V | VI |
|---|---|---|---|---|---|---|---|---|---|
| R | R' | A | B | A B | | A | B | | |
| ![N-ring structure] | " | 0.8 | 1.5 | 1.5 1.5 | 1.5 | 1.5 | >200 | 6.2 | 0.8 |
| NCCHS– / CH$_3$ | " | 0.4 | 0.8 | 1.5 3.1 | 1.5 | 1.5 | 400 | 0.8 | 0.4 |
| CH$_3$SO$_2$– | " | 0.8 | 3.1 | 1.5 1.5 | 1.5 | 0.8 | 400 | 12.5 | 0.4 |
| HOCH$_2$CH$_2$S– | " | 0.8 | 1.5 | 1.5 1.5 | 1.5 | 1.5 | 200 | 3.1 | 0.8 |
| C$_2$H$_5$SO$_2$– | " | 1.5 | 1.5 | 1.5 1.5 | 1.5 | 1.5 | >400 | 6.2 | 0.8 |
| NC(CH$_2$)$_2$SO$_2$– | " | 1.5 | 3.1 | 1.5 1.5 | 3.1 | 1.5 | 200 | 6.2 | 0.8 |
| NCCH$_2$S– | –OCONH$_2$ | 0.8 | 3.1 | 1.5 1.5 | 3.1 | 3.1 | >400 | 6.2 | 1.5 |
| " | –OCOCH$_3$ | 0.2 | 0.8 | 1.5 1.5 | 3.1 | 1.5 | >400 | 6.2 | 0.8 |
| CH≡CCH$_2$S– | [thiadiazole-S-CH$_3$] | 0.2 | 0.8 | 3.1 3.1 | 3.1 | 3.1 | 400 | 3.1 | 0.8 |
| N$_3$CH$_2$S– | " | 0.4 | 0.4 | 3.1 3.1 | 1.5 | 3.1 | >200 | 1.5 | 0.8 |
| [isoxazol-O–] | " | 0.2 | 0.8 | 3.1 3.1 | 3.1 | 3.1 | >400 | 6.2 | 1.5 |
| [isoxazol-S–] | " | 0.2 | 0.8 | 3.1 3.1 | 3.1 | 6.2 | >400 | 3.1 | 0.8 |
| N$_3$CH$_2$S– | –OCONH$_2$ | 0.2 | 1.5 | 3.1 6.2 | 3.1 | 3.1 | >400 | 3.1 | 1.5 |
| [isoxazol-S–] | –OCOCH$_3$ | 0.2 | 0.8 | 3.1 6.2 | 6.2 | 3.1 | >400 | 3.1 | 1.5 |
| CH≡CCH$_2$S– | " | 1.5 | 6.2 | 6.2 12.5 | 12.5 | 12.5 | >200 | 12.5 | 6.2 |
| N$_3$CH$_2$S– | " | 0.4 | 0.8 | 6.2 6.2 | 6.2 | 6.2 | >200 | 3.1 | 1.5 |

IA: *Staphylococcus aureus* 209 P
IB: *Staphylococcus aureus* (resistant to CP and PC)
IIA: *Escherichia coli* NIHJ
IIB: *Escherichia coli* 609 (resistant to CER)
III: *Shigella flexneri* Komagome
IVA: *Klebsiella neumoniae* 806
IVB: *Klebsiella neumoniae* 846 (resistant to CER)
V: *Proteus vulgaris*
VI: *Salmonella enteritidis* Gartner As shown above the compounds prepared by the process of this invention have excellent antibacterial activities against broad pathogenic microorganisms. These compounds can be administered orally or parenterally, for example, in the form of capsule, tablet and injection. Injection is usually preferred. The dosage unit depends upon the age, diseases and weight of patients, but a usual unit is in amounts from 250 mg to 3000 mg per day for adults and it is administered three or four times a day. But, if necessary, more than the above amount can be used.

This invention will be illustrated by the following examples and referential examples, but the scope of said invention is not limited by these examples.

REFERENTIAL EXAMPLE 1

Dicyclohexylammonium 3-acetoxymethyl-7α-methoxy-7β-(4-hydroxy-3,5-di-tert.-butylbenzylideneamino)-3-cephem-4-carboxylate To a suspension of 29.2g of 7β-amino-3-acetoxymethyl-3-cephem-4-carboxylic acid in 600 ml of methanol was added 18.1g of dicyclohexylamine and stirred at room temperature for 1 hour. To a semitransparent solution thus obtained was added 24.0g of 4-hydroxy-3,5-di-tert.-butylbenzaldehyde and stirred at room temperature for 2 hours and stirring was continued after adding 50g of molecular sieve 3A for further 5 hours. After filtration of the reaction mixture, the filtrate was condensed under reduced pressure to give a crystalline product which after an addition of isopropanol was collected by filtration. To a solution of 13.4g of dicyclohexylammonium 7β-(4-hydroxy-3,5-di-tert.-butylbenzylideneamino)-3-acetoxymethyl-3-cephem-4-carboxylate thus obtained in 200 ml of methanol was added dropwise 4.74g of 2,3-dichloro-5,6-dicyano-1,4-benzoquinone in 40 ml of methanol at −15° C, and after completion of the addition the stirring was continued for another 10 minutes at the same temperature and then 1g of 2,6-di-tert.-butyl-p-cresol was added to the reaction mixture. After stirring for another 10 minutes at 0° C, 5.60 ml of triethylamine was added to the solution, which was then condensed to about 50 ml under reduced pressure, diluted with 300 to 400 ml of chloroform and washed three times with the same volume of water. On drying over anhydrous magnesium sulfate the solvent was removed under reduced pressure, the residue extracted with ether, the extract was condensed and added with n-hexane to give a precipitate, which was collected by filtration affording 13.03g of the desired product as a yellow powder. Crystallization of this powder from n-hexane-chloroform yielded a pure sample melting at 139°–141° C.

| UV spectrum | $\lambda_{max}^{THF}$ | 283 nm |
|---|---|---|
| NMR spectrum | (CDCl$_3$) | δ ppm: |
| 8.38 | (singlet, —CH=N—) | |
| 7.57 | (singlet, phenyl with H at 2,6 positions) | |
| 5.52 | (broad, OH) | |
| 4.96 | (singlet, H at 6-position) | |
| 4.87 | (singlet, S-CH$_2$ at 3-position) | |
| 3.47 | (singlet, OCH$_3$) | |
| 3.23 | (double doublet, S-CH$_2$ at 2-position) | |
| 1.92 | (singlet, CH$_3$CO) | |
| 1.40 | (singlet, tert.-butyl) | |

Thin layer chromatography  R$_f$: 0.74
Elementary analysis for C$_{34}$H$_{57}$N$_3$O$_7$S · C$_6$H$_{14}$

| | C | H | N | S |
|---|---|---|---|---|
| Calculated: | 66.29; | 8.68; | 5.66; | 4.31 |
| Found: | 66.12; | 8.64; | 5.70; | 4.20 |

REFERENTIAL EXAMPLE 2

Lithium 3-acetoxymethyl-7β-(4-hydroxy-3,5-diisopropylbenzylideneamino)-7α-methoxy-3-cephem-4-carboxylate To a suspension of 544 mg of 3-acetoxymethyl-7β-amino-3-cephem-4-carboxylic acid in 8 ml of methanol was dropwise added under stirring a solution of 14 mg of lithium in 2 ml of methanol, and then added a solution of 412 mg of 3,5-diisopropylbenzaldehyde in 5 ml of chloroform. After the mixture was stirred overnight at room temperature, insoluble substances were removed by filtration and the filtrate was concentrated to dryness at room temperature under reduced pressure to give 930 mg of lithium 3-acetoxymethyl-7β-(4-hydroxy-3,5-diisopropylbenzylidenamino)-3-cephem-4-carboxylate as a yellowish brown powder. A solution of 467 mg of this lithium salt in 10 ml of tetrahydrofuran was cooled to −40° C and added a solution of 7 mg of lithium in 3 ml of methanol and subsequently 130 mg of tert.-butylhypochlorite. After further stirring for 40 minutes under cooling, the reaction mixture was condensed at room temperature and under a reduced pressure to give the desired product.

| NMR spectrum | (DMSO-d$_6$-CDCl$_3$) | δ ppm: |
|---|---|---|
| 8.48 | (singlet, —CH=N—) | |
| 7.55 | (singlet, phenyl with H at 2,6 positions) | |
| 5.08 | (singlet, H at 6-position) | |
| 5.03 | (broad singlet, S-CH$_2$ at 3-position) | |
| 3.57 | (singlet, OCH$_3$) | |
| 3.05–3.65 | (multiplet, S-CH$_2$ at 2-position) | |
| | CH(CH$_3$)$_2$ | |
| 2.07 | (singlet, CH$_3$CO) | |
| 1.27 | (doublet, CH(CH$_3$)$_2$) | |

Thin layer chromatography:  R$_f$: 0.44

REFERENTIAL EXAMPLE 3

Dicyclohexylammonium 7β-(4-hydroxy-3,5-di-tert.-butylbenzylideneamino)-3-(1-methyl-1H-tetrazol-5-yl)thiomethyl-7α-methoxy-3-cephem-4-carboxylate To a suspension of 3.28g of 7β-amino-3-(1-methyl-1H-tetrazol-5-yl)thiomethyl-3-cephem-4-carboxylic acid in 60 ml of methanol was added 1.81g of dicyclohexylamine and stirred for 1 hour, and then 2.40g of 4-hydroxy-3,5-di-tert.-butylbenzaldehyde, 20 ml of chloroform and 5g of molecular sieve 3A were added to the mixture and stirring was continued for further 5 hours. After filtration of the reaction mixture, the filtrate was concentrated to dryness under reduced pressure. The residue was extracted with chloroform-isopropylether (1:1) and the extract was condensed under reduced pressure and then diluted with a large excess of isopropylether. A precipitate thus produced was collected by filtration to give 7.04g of dicyclohexylammonium 7β-(4-hydroxy-3,5-di-tert.-butylbenzylideneamino)-3-(1-methyl-1H-tetrazol-5-yl)thiomethyl-3-cephem-4-carboxylate. To a solution of 1.45g of this compound in 20 ml of methanol was dropwise added at −15° C a solution of 475 mg of 2,3-dichloro-5,6-dicyano-1,4-benzoquinone in 4 ml of methanol. After stirring for 10 minutes at the same temperature, 100 mg of 2,6-di-tert.-butyl-p-cresol was added to the mixture and stirred for another 10 minutes at 0° C. After adding 0.56 ml of triethylamine the reaction mixture was condensed to about 10 ml under reduced pressure, diluted with 50 ml of chloroform, washed four times with the same volume of water, and dried over anhydrous sodium sulfate. The solvent was evaporated under reduced pressure and the residue was extracted with a mixture of chloroform-ether (3:7). The extract was condensed and subsequently added a large excess of n-hexane to deposit a precipitate, which was collected by filtration giving 926 mg of the desired product as a yellow powder.

| NMR spectrum | (CDCl$_3$) | δ ppm: |
|---|---|---|
| 8.47 | (singlet, —CH=N—) | |
| 7.61 | (singlet, 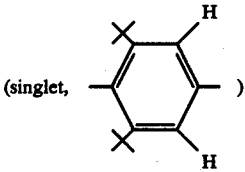) | |
| 5.60 | (broad, OH) | |
| 4.98 | (singlet, H at 6-position) | |
| 4.42 | (singlet, 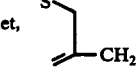 at 3-position) | |
| 3.80 | (singlet, N—CH$_3$) | |
| 3.48 | (singlet, OCH$_3$) | |
| around 3.4 | (double doublet,  at 2-position) | |
| 1.35 | (singlet, tert.-butyl) | |
| UV spectrum | $\lambda_{max}^{THF}$ | 285 nm |
| Thin layer chromatography | | R$_{fc}$: 0.72 |

REFERENTIAL EXAMPLE 4

Diisopropylammonium 7β-(4-hydroxy-3,5-di-tert.-butylbenzylideneamino)-3-(1-methyl-1H-tetrazol-5-yl)thiomethyl-7α-methoxy-3-cephem-4-carboxylate To a suspension of 16.5g of 7β-amino-3-(1-methyl-1H-tetrazol-5-yl)thiomethyl-3-cephem-4-carboxylic acid in 250 ml of methanol was added 4.545g of diisopropylamine, followed by stirring for 15 minutes. To the mixture was added 14.1g of 4-hydroxy-3,5-di-tert.-butylbenzaldehyde and 60 ml of chloroform and stirred for 2 hours. To the mixture was added 30g of anhydrous magnesium sulfate and stirred for 5 hours. The reaction mixture was filtered and the filtrate was concentrated to about 100 ml under reduced pressure. To the solution was added dropwise 10g of 2,3-dichloro-5,6-dicyano-1,4-benzoquinone in 50 ml of methanol at −15° C, followed by stirring at −15° C for 10 minutes. To the mixture was added 3.1g of 2,6-di-tert.-butyl-p-cresol and stirred for 10 minutes under ice-cooling. To the mixture were added 11.8 ml of diisopropylamine and 400 ml of benzene. The mixture was washed twice with water. The washings were extracted with 100 ml of benzene. The benzene solution was dried over anhydrous magnesium sulfate and concentrated to 150 ml. The mixture was poured into 500 ml of n-hexane. The precipitate produced was collected on a filtrate to give 19.1g of the desired product as yellow powder.

| UV spectrum | $\lambda_{max}^{THF}$ | 287 nm |
|---|---|---|
| NMR spectrum | (CDCl$_3$) | δ ppm: |
| 8.54 | (singlet, —CH=N—) | |
| 7.70 | (singlet, 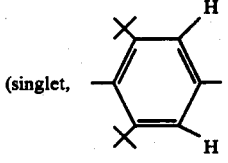) | |
| 5.66 | (broad, OH) | |
| 5.05 | (singlet, H at 6-position) | |
| 4.50 | (singlet  at 3-position) | |
| 3.85 | (singlet, N—CH$_3$) | |
| 3.54 | (singlet, O—CH$_3$) | |
| 3.63 and 3.36 | (double doublet,  at 2-position) | |
| 1.43 | (singlet, tert.-butyl) | |

EXAMPLE 1

3-Acetoxymethyl-7β-cyanomethylthioacetamido-7α-methoxy-3-cephem-4-carboxylic acid To a solution of 520 mg of lithium 3-acetoxymethyl-7β-(4-hydroxy-3,5-diisopropylbenzylideneamino)-7α-methoxy-3-cephem-4-carboxylate prepared by the method described in the Referential example 2 in 4 ml of methanol was added 185 mg of Girard T reagent under stirring and cooling in an ice-salt bath. After further stirring for 10 minutes under cooling, solutions of 450 mg of N,N-diethylaniline in 1 ml of methanol and 320 mg of cyanomethylthioacetyl chloride in 1 ml of dichloroethane were dropwise added successively. The stirring was continued for another 30 minutes under cooling in an ice-salt bath. To the reaction mixture thus obtained was added 20 ml of 0.2 N-hydrochloric acid, the mixture stirred for 2–3 minutes and extracted with ethyl acetate. The extract was washed with water and the acidic substance in the extract was separated by shaking three times with aqueous 10% dipotassium hydrogen phosphate. The aqueous layer was washed two times with ethyl acetate and adjusted to pH 2.0 by adding 10% hydrochloric acid. This solution was extracted again with ethyl acetate, the extract dried over anhydrous magnesium sulfate and the solvent removed by evaporation. The residue was washed with cyclohexane and a small amount of ether yielded 95 mg of 3-acetoxymethyl-7β-cyanomethylthioacetamido-7α-methoxy-3-cephem-4-carboxylic acid.

| NMR spectrum | (CD$_3$CN) | δ ppm: |
|---|---|---|
| 2.02 | (singlet, —OCOCH$_3$ at 3-position) | |

-continued

| 3.32–3.55 | (quartet, S\⟨H H at 2-position) |
| --- | --- |
| 3.42, 3.60 | (singlet indivisually, —CH$_2$SCH$_2$CO—, —CH$_2$SOH$_2$CO— at 7-position) |
| 3.52 | (singlet, OCH$_3$ at 7-position) |
| 4.76–5.06 | (quartet, ⟩—CH$_2$— at 3-position) |
| 5.06 | (singlet, H\⟩—N⟨ at 6-position) |
| IR spectrum (Nujol) | $\nu$ cm$^{-1}$: 1775 |
| UV spectrum | $\lambda_{max}$ 247, 267 nm |

EXAMPLE 2

7β-Cyanomethylthioacetamido-7α-methoxy-3-(1-methyl-1H-tetrazol-5-yl)thiomethyl-3-cephem-4-carboxylic acid To a solution of 35.45g of dicyclohexylammonium 7α-methoxy-7β-(4-hydroxy-3,5-di-tert.-butylbenzylideneamino)-3-(1-methyl-1H-tetrazol-5-yl)thiomethyl-3-cephem-4-carboxylate prepared by the procedures described in the Referential example 3 in 150 ml of methylene chloride was added 8.38g of phenylacetic acid hydrazide and the mixture was stirred for 75 minutes at room temperature. After the mixture was cooled to −15° C, 22.4 ml of diethylaniline and 21.0g of cyanomethylthioacetyl chloride was added and the mixture stirred for 40 minutes under ice-cooling. The reaction mixture was concentrated under reduced pressure, and diluted with ethyl acetate to deposit a crystalline substance, which was collected by filtration. The ethyl acetate solution was washed with a small amount of water and subsequently extracted two times with aqueous 10% dipotassium hydrogen phosphate solution. To the aqueous phase was added ethyl acetate, the mixture was adjusted to pH 2.5 by 3N-hydrochloric acid and shaken well. The aqueous layer separated was, after saturation with sodium chloride, extracted repeatedly with ethyl acetate. The combined extract was washed two times with an aqueous saturated sodium chloride solution, once with a small amount of water and dried over anhydrous sodium sulfate. Removal of the solvent under reduced pressure afforded 16.04g of 7β-cyanomethylthioacetamido-7α-methoxy-3-(1-methyl-1H-tetrazol-5-yl)thiomethyl-3-cephem-4-carboxylic acid as a syrupy substance.

| NMR spectrum | (CD$_3$CN + D$_2$O) $\delta$ ppm: |
| --- | --- |
| 3.50 | (singlet, OCH$_3$ at 7-position) |
| 3.5–3.7 | (multiplet, S\⟨H H at 2-position) |
| 3.60, 3.70 | (singlet indivisually, —CH$_2$SCH$_2$CO—, —CH$_2$SCH$_2$CO—at 7-position) |
| 3.98 | (singlet, N—OH$_3$ at 3-position in tetrazol) |
| 4.3–4.6 | (quartet, ⟩—CH$_2$— at 3-position) |
| 5.10 | (singlet, H\⟩—N⟨ at 6-position) |

EXAMPLE 3

3-Acetoxymethyl-7β-cyanomethylthioacetamido-7α-methoxy-3-cephem-4-carboxylic acid To a solution of 14.0g of dicyclohexylammonium 3-acetoxymethyl-7α-methoxy-7β-(4-hydroxy-3,5-di-tert.-butylbenzylideneamino)-3-cephem-4-carboxylate prepared by the method shown in the Referential example 1 in 70 ml of methylene chloride was added 3.60g of phenylacetic acid hydrazide and the mixture was stirred for 70 minutes at room temperature. After cooling the reaction mixture to −15° C, 9.51 ml diethylaniline and 9.0g of cyanomethylthioacetyl chloride were added and the mixture was stirred for 40 minutes under ice-cooling. After addition of 50 ml of methanol, the reaction mixture was stirred for another 2 hours at room temperature, subsequently concentrated under reduced pressure and diluted with ethyl acetate to deposit a crystalline material which was removed by filtration. The ethyl acetate solution was washed with a small amount of water and then extracted three times with aqueous 10% sodium phosphate solution. The combined extract was adjusted to pH 2.5 by 3N-hydrochloric acid and an oily substance separated was extracted with ethyl acetate. The aqueous layer was thoroughly extracted with ethyl acetate. The combined ethyl acetate extract was washed with water. The washing was again extracted with ethyl acetate. The ethyl acetate solution was dried over anhydrous sodium sulfate and the solvent was removed by distillation under reduced pressure to give 6.53g of 3-acetoxymethyl-7β-cyanomethylthioacetamido-7α-methoxy-3-cephem-4-carboxylic acid as a syrupy substance.

Following the procedure of the above Example 3, but replacing the cyanomethylthioacetyl chloride with 3-isoxazolylthioacetyl chloride (10.9g), there was prepared 3-acetoxymethyl-7β-(3-isoxazolylthio)acetamido-7α-methoxy-3-cephem-4-carboxylic acid (6.70g).

EXAMPLE 4

3-Acetoxymethyl-7β-azidomethylthioacetamido-7α-methoxy-3-cephem-4-carboxylic acid By using dicyclohexylammonium 3-acetoxymethyl-7α-methoxy-7β-(4-hydroxy-3,5-di-tert.-butylbenzylideneamino)-3-cephem-4-carboxylate prepared by the method described in the referential example 1 as a starting material and according to the procedures described in the Example 3 using, instead of the cyanomethylthioacetyl chloride, 9.93g of azidomethylthioacetyl chloride, there was obtained 7.37g of 3-acetoxymethyl-7β-azidomethylthioacetamido-7α-methoxy-3-cephem-4-carboxylic acid.

| IR spectrum (Nujol) | $\nu_{max}$ cm$^{-1}$: 3280, 2110, 1775, 1730, 1720(sh), 1690 |
| --- | --- |
| UV spectrum (EtOH) | $\lambda_{max}$ nm: 247($\epsilon$ = 7,800), 269($\epsilon$ = 8,000) |
| NMR spectrum (CMSO-d$_6$) | $\delta$ ppm: |
| 2.00 | (3H, singlet, OCOCH$_3$) |
| 3.3–3.6 | (2H, quartet, H$_2$ at 2-position) |
| 3.40 | (5H, singlet, OCH$_3$ at 7-position and SCH$_2$CO) |
| 4.51 | (2H, singlet, N$_3$CH$_2$S—) |
| 4.69–4.98 | (2H, quartet, CH$_2$OCO— at 3-position) |
| 5.14 | (1H, singlet, H at 6-position) |

Elementary analysis for C$_{14}$H$_{17}$N$_5$O$_7$S$_2$

| | C | H | N |
| --- | --- | --- | --- |
| Calculated: | 38.97; | 3.97; | 16.23 |
| Found: | 39.08; | 4.21; | 15.88 |

EXAMPLE 5

3-Acetoxymethyl-7β-(3-isoxazolyloxy)acetamido-7α-methoxy-3-cephem-4-carboxylic acid By using dicyclohexylammonium 3-acetoxymethyl-7α-methoxy-7β-(4-hydroxy-3,5-di-tert.-butylbenzylideneamino)-3-cephem-4-carboxylate prepared by the method described in the Referential example 1 as a starting material and according to the procedures described in the Example 3 using, instead of the cyanomethylthioacetyl chloride, 9.7g of 3-isoxazolyloxyacetyl chloride, there was obtained 6.57g of 3-acetoxymethyl-7β-(3-isoxazolyloxy)acetamido-7α-methoxy-3-cephem-4-carboxylic acid.

Thin layer chromatography (silica gel):
Developing solvent: methanol:chloroform = 1:2
$R_f = 0.28$
IR spectrum (Nujol) $\nu_{max}$ cm$^{-1}$:
   3500, 3270, 1780, 1725, 1700 (sh)
UV spectrum (a buffer solution of pH 6.8) $\lambda_{max}$ nm:
   264 ($\epsilon = 8,300$)
NMR spectrum (DMSO-d$_6$) δ ppm:
9.56     (1H, singlet, CON$\underline{H}$ at 7-position)

8.70     (1H, doublet, 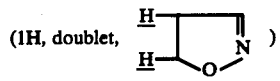 )

6.31     (1H, doublet, 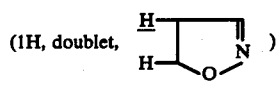 )

5.30     (1H, singlet, C—$\underline{H}$ at 6-position)
5.12–4.18     (2H, double doublet, —C$\underline{H}_2$O at 3-position)
4.82     (2H, singlet, —OC$\underline{H}_2$CO)
3.85–3.14     (2H, double doublet, —C$\underline{H}_2$— at 2-position)
3.41     (3H, singlet, OC$\underline{H}_3$ at 7-position)
2.00     (3H, singlet, COC$\underline{H}_3$ at 3-position)

Elementary analysis for $C_{16}H_{17}O_9N_3S$

| | C | H | N |
|---|---|---|---|
| Calculated: | 44.97; | 4.01; | 9.83 |
| Found: | 45.12; | 4.36; | 9.66 |

EXAMPLE 6

3-Acetoxymethyl-7α-methoxy-7β-propargylthioacetamido-3-cephem-4-carboxylic acid By using dicyclohexylammonium 3-acetoxymethyl-7α-methoxy-7β-(4-hydroxy-3,5-di-tert.-butylbenzylideneamino)-3-cephem-4-carboxylate prepared by the method described in the Referential example 1 as a starting material and according to the procedures described in the Example 3 using, instead of the cyanomethylthioacetyl chloride, 8.85g of propargylthioacetyl chloride there was obtained 6.50g of 3-acetoxymethyl-7α-methoxy-7β-propargylthioacetamido-3-cephem-4-carboxylic acid.

Melting point: 122–124° C (decomp.)
IR spectrum (KBr) $\nu_{max}$ cm$^{-1}$:
   3260, 1775, 1730, 1705, 1660
UV spectrum (EtOH) $\lambda_{max}$ nm:
   245 ($\epsilon = 7,800$), 268 ($\epsilon = 8,200$)
NMR spectrum (DMSO-d$_6$) δ ppm:
1.98     (3H, singlet, OCOC$\underline{H}_3$)
3.05     (1H, triplet, $\underline{H}$C≡C—)
3.2–3.5     (6H, multiplet, H$_2$ at 2-position and —C$\underline{H}_2$SC$\underline{H}_2$—)
3.36     (3H, singlet, OC$\underline{H}_3$ at 7-position)
4.9–4.6     (2H, quartet, —C$\underline{H}_2$OCO at 3-position)
5.05     (1H, singlet, $\underline{H}$ at 6-position)

Elementary analysis for $C_{16}H_{18}O_7N_2S_2$

| | C | H | N |
|---|---|---|---|
| Calculated: | 46.36; | 4.38; | 6.76 |
| Found: | 46.21; | 4.30; | 6.55 |

EXAMPLE 7

7β-Cyanomethylthioacetamido-7α-methoxy-3-(1-methyl-1H-tetrazol-5-yl)thiomethyl-3-cephem-4-carboxylic acid To a solution of 1.5g of trimethylbenzylammonium 7β-(4-hydroxy-3,5-di-tert.-butylbenzylideneamino)-7α-methoxy-3-(1-methyl-1H-tetrazol-5-yl)thiomethyl-3-cephem-4-carboxylate in 5 ml of dichloroethane was added a solution of 0.8g of phenylhydrazine in 1 ml of dichloroethane under stirring at 0°–5° C. After 30 minutes 40 ml of cyclohexane was added to the reaction mixture, a precipitate produced was collected by filtration and washed with a mixture of cyclohexane:ether (1:1) to afford 1.03g of trimethylbenzylammonium 7β-amino-7α-methoxy-3-(1-methyl-1H-tetrazol-5-yl)thiomethyl-3-cephem-4-carboxylate.

Thin layer chromatography (silica gel):
Developing solvent:chloroform:methanol (3:1)
$R_f = 0.1$ The ammonium salt thus obtained may be used per se for the next step, but chromatography using dried silica gel eluted with chloroform:methanol (10:1) and Sephadex LH-20 eluted with chloroform:methanol (10:1) afforded 0.2g of a purified free carboxylic acid.

NMR spectrum (DMSO-d$_6$) δ ppm:
3.22     (3H, singlet, OC$\underline{H}_3$ at 7-position)
3.40     (2H, quartet, $\underline{H}_2$ at 2-position)
3.80     (3H, singlet, N—CH$_3$)
4.15     (2H, broad singlet, —C$\underline{H}_2$S at 3-position)
4.64     (1H, singlet, $\underline{H}$ at 6-position)
IR spectrum (Nujol) $\nu_{max}$ cm$^{-1}$:
   3300–3400 (NH$_2$), 1740–1760 (β-lactam)

To a solution of 1.03g of trimethylbenzylammonium 7β-amino-7α-methoxy-3-(1-methyl-1H-tetrazol-5-yl)thiomethyl-3-cephem-4-carboxylate prepared as described above in 14 ml of dichloroethane was added a solution of 0.9g of N,N-diethylaniline in 2 ml of dichloroethane and subsequently a solution of 0.9g of cyanomethylthioacetyl chloride in 2 ml of dichloroethane under stirring and cooling with a freezing mixture. After stirring for 40 minutes 20 ml of methanol was added to the reaction mixture and stirring continued for another 1 hour. The reaction mixture was concentrated at room temperature, the residue dissolved in 10 ml of chloroform and 30 ml of aqueous 10% dipotassium hydrogen phosphate and stirred for 10 minutes. The chloroform layer separated was extracted two times with aqueous 10% dipotassium hydrogen phosphate solution. The combined aqueous extract was washed two times with ethyl acetate and adjusted to pH 2.0 by 3N-hydrochloric acid. An oily substance separated was extracted with ethyl acetate, the extract washed once with water, dried over anhydrous magnesium sulfate, and the solvent was removed to give 706 mg of 7β-cyanomethylthioacetamido-7α-methoxy-3-(1-methyl-1H-tetrazol-5-yl)thiomethyl-3-cephem-4-carboxylic acid as a pale brown powder. A solution of this crude product in 4 ml of ethyl acetate was ice-cooled and added with 0.45 ml of dicyclohexylamine to form a crystalline product, which, after addition of ether, was collected by filtration and recrystallized from ethanol to give 473 mg of a dicyclohexylamine salt as colorless crystals melting at 152° C with decomposition. To this crystalline salt was added about 10 ml of water and 20 ml of ethyl acetate and the mixture was adjusted under stirring to pH 2-1.5 by addition of 10% hydrochloric acid. After shaking in a separatory funnel the ethyl acetate layer was separated, the aqueous layer extracted three times with ethyl acetate, the combined extract washed once with water, dried over anhydrous magnesium sulfate, and the solvent was removed to give 240 mg of 7β-cyanomethylthio-acetamido-7α-methoxy-3-(1-methyl-1H-tetrazol-5-yl)thiomethyl-3-cephem-4-carboxylic acid as a nearly white powder.

EXAMPLE 8

7β-Propargylthiomethylacetamido-7α-methoxy-3-(1-methyl-1H-tetrazol-5-yl)thiomethyl-3-cephem-4-carboxylic acid To a solution of 6.76g of diisopropylammonium 7α-methoxy-7β-(4-hydroxy-3,5-di-tert.-butylbenzylideneamino)-3-(1-methyl-1H-tetrazol-5-yl)thiomethyl-3-cephem-4-carboxylate prepared by the method described in the Referential example 4 in 25 ml of methylene chloride was added 1.08g of phenylhydrazine, followed by stirring under ice-cooling for 20 minutes. The reaction mixture was cooled to −15° C and to the mixture were added 4.80 ml of diethylaniline and 4.45g of propargylthioacetyl chloride. The mixture was stirred under ice-cooling for 40 minutes. To the mixture was added 30 ml of methanol and the mixture was stirred for 2 hours at room temperature. The reaction mixture was concentrated to dryness under reduced pressure and the residue was dissolved in ethyl acetate. The solution was washed with a small amount of water and extracted three times with a 10% aqueous disodium hydrogen phosphate. The extracts were combined and adjusted to pH 2.5 by addition of 3N-hydrochloric acid. An oily substance produced was extracted with ethyl acetate. The extract was washed with water and dried over anhydrous sodium sulfate. The solvent was distilled off to give 2.72g of the desired product as a syrupy substance.

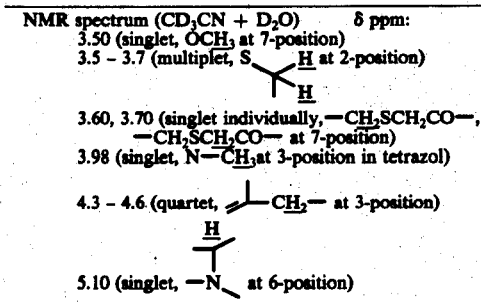

NMR spectrum (CD₃CN + D₂O)   δ ppm:
3.50 (singlet, OCH₃ at 7-position)
3.5 – 3.7 (multiplet, S—CH— H at 2-position)

3.60, 3.70 (singlet individually,—CH₂SCH₂CO—, —CH₂SCH₂CO— at 7-position)
3.98 (singlet, N—CH₃ at 3-position in tetrazol)

4.3 – 4.6 (quartet, —CH₂— at 3-position)

5.10 (singlet, —N at 6-position)

Following the procedure of the above Example 8, but replacing the propargylthioacetyl chloride with (sydnon-3)acetyl chloride (4.89g),
1-cyanoethylthioacetyl chloride (4.90g),
methylsulfonylacetyl chloride (4.69g),
ethylsulfonylacetyl chloride (5.11g),
cyanoethylsulfonylacetyl chloride (5.86g),
propargylthioacetyl chloride (3.50g),
azidomethylthioacetyl chloride (3.70g),
3-isoxazolyloxyacetyl chloride (4.85g) and
3-isoxazolylthioacetyl chloride (5.41g), there were prepared 7β-(sydnon-3)acetamido-7α-methoxy-3-(1-methyl-1H-tetrazol-5-yl)thiomethyl-3-cephem-4-carboxylic acid (2.67g),
7β-(1-cyanoethyl)acetamido-7α-methoxy-3-(1-methyl-1H-tetrazol-5-yl)thiomethyl-3-cephem-4-carboxylic acid (2.91g),
7β-methylsulfonylacetamido-7α-methoxy-3-(1-methyl-1H-tetrazol-5-yl)thiomethyl-3-cephem-4-carboxylic acid (2.92g),
7β-ethylsulfonylacetamido-7α-methoxy-3-(1-methyl-1H-tetrazol-5-yl)thiomethyl-3-cephem-4-carboxylic acid (2.85g),
7β-cyanoethylsulfonylacetamido-7α-methoxy-3-(1-methyl-1H-tetrazol-5-yl)thiomethyl-3-cephem-4-carboxylic acid (3.05g),
7α-methoxy-3-(1-methyl-1H-tetrazol-5-yl)thiomethyl-7β-propargylmethylthioacetamido-3-cephem-4-carboxylic acid (2.36g),
7β-(3-isoxazolyloxy)acetamido-7α-methoxy-3-(1-methyl-1H-tetrazol-5-yl)thiomethyl-3-cephem-4-carboxylic acid (2.60g) and
7β-(3-isoxazolylthio)acetamido-7α-methoxy-3-(1-methyl-1H-tetrazol-5-yl)thiomethyl-3-cephem-4-carboxylic acid (2.91g).

EXAMPLE 9

7β-(2-Hydroxyethylthio)acetamido-7α-methoxy-3-(1-methyl-1H-tetrazol-5-yl)thiomethyl-3-cephem-4-carboxylic acid Following the procedure of the above Example 8, but replacing the propargylthioacetyl chloride with tetrahydropyranyl-2-oxyethylthioacetyl chloride (7.18g), there was prepared 2.52g of 7β-(tetrahydropyranyl-2-oxyethylthioacetamido)-7α-methoxy-3-(1-methyltetrazol-5-ylthio)methyl-3-cephem-4-carboxylic acid as a pale yellow powder. The powder was dissolved in 10 ml of anisole and to the solution was added 10 ml of trifluoroacetic acid under ice-cooling, followed by stirring at room temperature for 5 minutes. The solvent was distilled off and the residue was dissolved in a mixture of 200 ml of ethyl acetate and 50 ml of a 10% aqueous dipotassium hydrogen phosphate. The aqueous layer was washed with 100 ml of ethyl acetate, adjusted to pH 2.0, saturated with sodium chloride and extracted with ethyl acetate. The extract was dried and the solvent was distilled off. The residue was purified by preparative thin layer chromatography to give 670 mg of the desired product as amorphous powder.

What is claimed is:
1. A process for preparing a 7α-methoxy-3-cephem-4-carboxylic acid having the formula

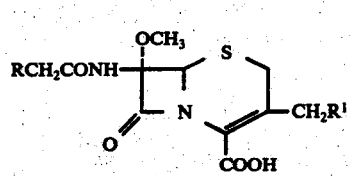

(I)

wherein R represents cyanomethylthio, 1-cyanoethylthio, azidomethylthio, propargylthio, 2-hydroxyethylthio, 2,3-dihydroxypropylthio, methylsulfonyl, ethylsulfonyl, cyanoethylsulfonyl, 3-isoxazolyloxy, 3-isoxazolylthio, 2-(1,3,4-thiadiazolyl)thio, 2-imidazolythio or sydnon-3-yl nd R¹ is acetoxy, carbamoyloxy or 1-methyl-1H-tetrazol-5-ylthio or a salt with the carboxyl group thereof which comprises the steps of contacting a 7β-benzylidenemino-7α-methoxy-3-cephem-4-carboxylic acid having the formula (II)

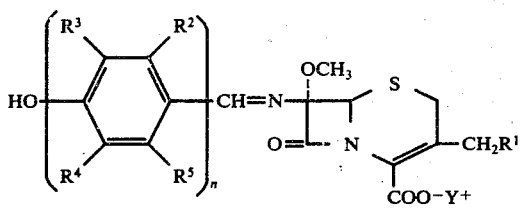

wherein $R^1$ is the same as defined above, $R^2$, $R^3$, $R^4$ and $R^5$ may be the same or different and each represents hydrogen atom, an alkyl having 1–4 carbon atoms, an alkoxy having 1–4 carbon atoms, or a halogen atom, or $R^2$ and $R^3$ or $R^4$ and $R^5$ may be linked together to form a saturated, unsaturated or aromatic ring, $n$ is an integer of 1 or 2 and $Y^+$ is a cation selected from the group consisting of an alkali metal ion and an ammonium ion having the formula

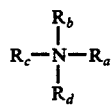

wherein $R_a$, $R_b$, $R_c$ and $R_d$ can be the same or different, and each is selected from the group consisting of hydrogen alkyl having from 1 to 8 carbon atoms, cyclopentyl, cyclohexyl, cycloheptyl, phenyl, phenylalkyl wherein the alkyl has from 1 to 4 carbon atoms, $R_a$ and $R_b$ can be linked together with said N to form a saturated heterocyclic ring, and $R_a$, $R_b$ and $R_c$ can be linked together with said N to form a heterocyclic ring, with a hyrazine to give a 7-amino-7-methoxy-3-cephem-4-carboxylic acid having the formula

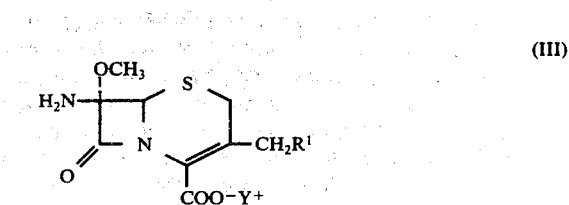

(III)

wherein $R^1$ and $Y^+$ are the same as defined above, and reacting the latter compound with a compound selected from the group consisting of a carboxylic acid having the formula

RCH$_2$COOH    (IV)

wherein R is the same as defined above, an acid halide of (IV), an azide of (IV), an acid anhydride of (IV), a p-nitrophenyl ester of (IV), cyanomethyl ester of (IV) and a phthalimide ester of (IV).

2. The process of claim 1 in which $R^2$ and $R^5$ are hydrogen atom and $R^3$ and $R^4$ are isopropyl or tert.-butyl and n is 1 and $Y^+$ is sodium, lithium, tert.-butylammonium, tert.-octylammonium, dicyclohexylammonium, dissopropylammonium, triethylammonium or trimethylbenzylammonium ion.

3. The process of claim 1 in which the hyrazine is phenylacetic acid hydrazine, phenylhydrazine, pyridylacetohydrazide chloride or trimethylaminoacetohydrazide chloride.

4. The process of claim 1 in which the halide of the carboxylic acid (IV) is a chloride of the carboxylic acid (IV).

5. The process of claim 1 in which the reaction of the compound (III) with the halide of the carboxylic acid (IV) is carried out in the presence of an alkali metal hydroxide, carbonate or hydrogen carbonate, or tertiary amine.

6. The process of claim 5, in which the said reaction is carried out in the presence of a tertiary amine.

7. The process of claim 6 in which the tertiary amine is diethylaniline.

* * * * *

UNITED STATES PATENT OFFICE
CERTIFICATE OF CORRECTION

Patent No. 4,051,129          Dated September 27, 1977

Inventor(s)   BUNJI SHIMIZU et al

It is certified that error appears in the above-identified patent and that said Letters Patent are hereby corrected as shown below:

Column 1, line 26:  rewrite "groups" as ---group---.

Column 5, line 30:  delete "7β-(syndon-3)-" and re-insert at the beginning of a new line as ---7β-(sydnon-3)- ---.

Column 12, line 6:  rewrite "filtrate" as ---filter---.

Column 13, line 7:  rewrite "$CH_2SOH_2CO$" as ---$CH_2SCH_2CO$---.

Column 13, line 61:  rewrite "$N-OH_3$" as ---$N-CH_3$---.

Column 18, line 66 (Claim 1):  rewrite "imidazolythio" ---imidazolylthio---.

Column 19, line 2 (Claim 1):  rewrite "benzylidenemino" ---benzylideneamino---.

UNITED STATES PATENT OFFICE
CERTIFICATE OF CORRECTION

Patent No. 4,051,129　　　　　　　　Dated September 27, 1977

Inventor(s) BUNJI SHIMIZU et al

It is certified that error appears in the above-identified patent and that said Letters Patent are hereby corrected as shown below:

Column 19, line 40 (Claim 1): rewrite "hyrazine" as ---hydrazine---.

Column 20, line 26 (Claim 4): rewrite "hyrazine" as ---hydrazine---.

Signed and Sealed this

Eighth Day of August 1978

[SEAL]

Attest:

RUTH C. MASON
*Attesting Officer*

DONALD W. BANNER
*Commissioner of Patents and Trademarks*